US008911088B2

(12) United States Patent
Van Saarloos et al.

(10) Patent No.: US 8,911,088 B2
(45) Date of Patent: Dec. 16, 2014

(54) OPTICAL APPARATUS FOR RETINAL PHOTOGRAPHY

(75) Inventors: Paul Van Saarloos, Balcatta (AU); Michael Same, Balcatta (AU)

(73) Assignee: CV Laser Pty Ltd, Osborne Park, Western Australia (AU)

( * ) Notice: Subject to any disclaimer, the term of this patent is extended or adjusted under 35 U.S.C. 154(b) by 166 days.

(21) Appl. No.: 13/258,625

(22) PCT Filed: Mar. 25, 2010

(86) PCT No.: PCT/AU2010/000350
§ 371 (c)(1),
(2), (4) Date: Apr. 11, 2012

(87) PCT Pub. No.: WO2010/108228
PCT Pub. Date: Sep. 30, 2010

(65) Prior Publication Data
US 2013/0050644 A1    Feb. 28, 2013

(30) Foreign Application Priority Data

Mar. 25, 2009    (AU) ............................. 2009901271

(51) Int. Cl.
*A61B 3/14*    (2006.01)
(52) U.S. Cl.
CPC ....................................... *A61B 3/14* (2013.01)
USPC ........................................................ 351/206
(58) Field of Classification Search
USPC ................................................. 351/206, 218
See application file for complete search history.

(56) References Cited

U.S. PATENT DOCUMENTS

| 5,784,147 | A |  | 7/1998 | Volk |  |
|---|---|---|---|---|---|
| 5,861,939 | A |  | 1/1999 | Heacock |  |
| 2003/0025876 | A1 |  | 2/2003 | Nanjo |  |
| 2007/0291225 | A1 | * | 12/2007 | Suzuki | 351/206 |
| 2008/0231803 | A1 | * | 9/2008 | Feldon et al. | 351/206 |
| 2008/0259274 | A1 |  | 10/2008 | Chinnock |  |
| 2009/0201467 | A1 | * | 8/2009 | Smith et al. | 351/206 |

FOREIGN PATENT DOCUMENTS

| EP |  | 0 048 181 | A2 | 3/1982 |
|---|---|---|---|---|
| EP |  | 1 870 025 | A1 | 12/2007 |
| WO | WO 2006/118560 |  | A2 | 11/2006 |

OTHER PUBLICATIONS

International Search Report for corresponding International Patent Application No. PCT/AU2010/000350 mailed May 24, 2010, 4 pages.
DeHoog, E. et al. "Fundus Camera systems: a comparative analysis", Applied Optics, vol. 48, No. 2, Jan. 10, 2009, pp. 221-228.

* cited by examiner

*Primary Examiner* — Scott J Sugarman
*Assistant Examiner* — Mustak Choudhury
(74) *Attorney, Agent, or Firm* — Merchant & Gould P.C.

(57) ABSTRACT

Optical apparatus for retinal photography includes a housing (20) fitted to or adapted to be fitted to a camera and defining an optical path (21) that is aligned with the camera lens assembly and extends therefrom to a nose region (25) of the housing. The housing has a projecting handle (24) dimensioned and profiled to be grasped by hand for holding the apparatus in one hand. A plurality of lens components (42, 44) in the optical path and an illumination source (46) co-operate to illuminate a retina of an eye in front of the nose region of the housing, and to image the illuminated retina at the image sensor of the camera.

24 Claims, 2 Drawing Sheets

OPTICAL APPARATUS FOR RETINAL PHOTOGRAPHY

This application is a National Stage Application of PCT/AU2010/000350, filed 25 Mar. 2010, which claims benefit of Serial No. 2009901271, filed 25 Mar. 2009 in Australia and which applications are incorporated herein by reference. To the extent appropriate, a claim of priority is made to each of the above disclosed applications.

FIELD OF THE INVENTION

This invention relates generally to retinal photography and particularly to optical apparatus for retinal photography that is particularly suitable as a portable device for use in obtaining digital images of the retina, human or animal.

BACKGROUND OF THE INVENTION

Ophthalmic examination of the retina is a valuable diagnostic tool in the early stages detection of glaucoma, diabetes, cataracts and macular degeneration, among other conditions. It is recognised that the reliability of detection of both diabetic retinopathy and more general referable retinopathy is enhanced by the use of retinal photographs. At present, retinal photography is generally mydriatic, that is requires the use of drugs or drops to dilate the pupil of the eye, and involves the subject being seated at a quite specific location adjacent a table or other structure fitted with the camera equipment. These limitations apply equally to some retinal cameras described as "portable" but which are not portable in the sense that they are lightweight and can be easily brought to the subject.

It is an objection of the present invention to provide improvements that will allow retinal photography to be more user friendly for both subject and clinician, including preferably being adapted to non-mydriatic performance and preferably being truly portable.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect, the invention provides optical apparatus for retinal photography comprising a housing fitted to or adapted to be fitted to a camera and defining an optical path aligned with the camera lens assembly and extending therefrom to a nose region of the housing, said housing having a projecting handle dimensioned and profiled to be grasped by hand for holding the apparatus in one hand, the apparatus further comprising a plurality of lens components in said optical path and illumination means that co-operate to illuminate a retina of an eye in front of said nose region of the housing, and to image the illuminated retina at the image sensor of the camera.

The lens components preferably include first and second lens elements mounted at spaced locations in the optical path respectively nearer the camera lens assembly and further from the camera lens assembly. The second lens element may typically be a double aspheric lens.

The illumination means is advantageously a solid state light source mounted in the optical path between said first and second lens elements but closer to the first lens element, in a manner whereby light emitted by the solid state light source is focused at or near the pupil of an eye in front of said nose region of the housing and thereby illuminates the retina of the eye.

Preferably, said first and second lens elements cooperate to limit the field of view of the camera to the pupil area of said eye.

In a second aspect, the invention further provides optical apparatus for retinal photography, comprising:
a housing fitted or adapted to be fitted to a camera and defining an optical path aligned with the camera lens assembly and extending therefrom to a nose region of the housing;
first and second lens elements mounted at spaced locations in the optical path respectively nearer the camera lens assembly and further from the camera lens assembly; and
a solid state light source mounted in the optical path between said first and second lens elements but closer to the first lens element, in a manner whereby light emitted by the solid state light source is focused at or near the pupil of an eye in front of said nose region of the housing and thereby illuminates the retina of the eye;
wherein said first and second lens elements cooperate to limit the field of view of the camera to the pupil area of said eye, and to image the illuminated retina at the image sensor of the camera.

Conveniently, the optical apparatus further includes trigger means to flash the illumination means or solid state light source as the camera operates to capture said image.

The apparatus preferably includes the camera. The camera is advantageously a digital camera.

The housing fitted or adapted to be fitted to the camera is preferably of such a size when fitted to the camera that it is able to be held in one hand and thereby brought to a subject and held and operated in front of an eye of the subject.

The second lens element may typically be a double aspheric lens.

The apparatus may further include control means including said trigger means arranged whereby the trigger means is actuable to operate the camera and the camera flash simultaneously with said flashing of the solid state light source.

The housing preferably comprises a generally tubular or tubular/conical portion that defines the optical path and encloses the first and second lens elements and the solid state light source, and a depending handle portion incorporating the trigger and dimensioned and profiled to be grasped by one hand.

The generally tubular or tubular/conical portion of the housing may typically include a window at the end thereof remote from the camera, which window conveniently comprises the second lens element.

Preferably, the solid state light source, which may typically comprise a light emitting diode (LED), is mounted at or near the optical axis defined by the first and second lenses, and is preferably mounted on a narrow stalk or the like to minimise the obstruction of light returning to the camera.

The apparatus may further include one or more batteries, preferably a single battery unit for powering the solid state light source, the digital camera and associated electronics.

The first lens is preferably a convex lens.

An adjustable iris is advantageously provided between the light source and the second lens. This iris is preferably angled to divert reflections from it returning to the camera and may have an aperture that is elliptical in effect, in order to match the aspect ratio of the camera image, or is a slit of adjustable aperture size and shape.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

The invention will now be described, by way of example only, with reference to the accompanying drawings, in which.

EMBODIMENTS OF THE INVENTION

Figure 1:
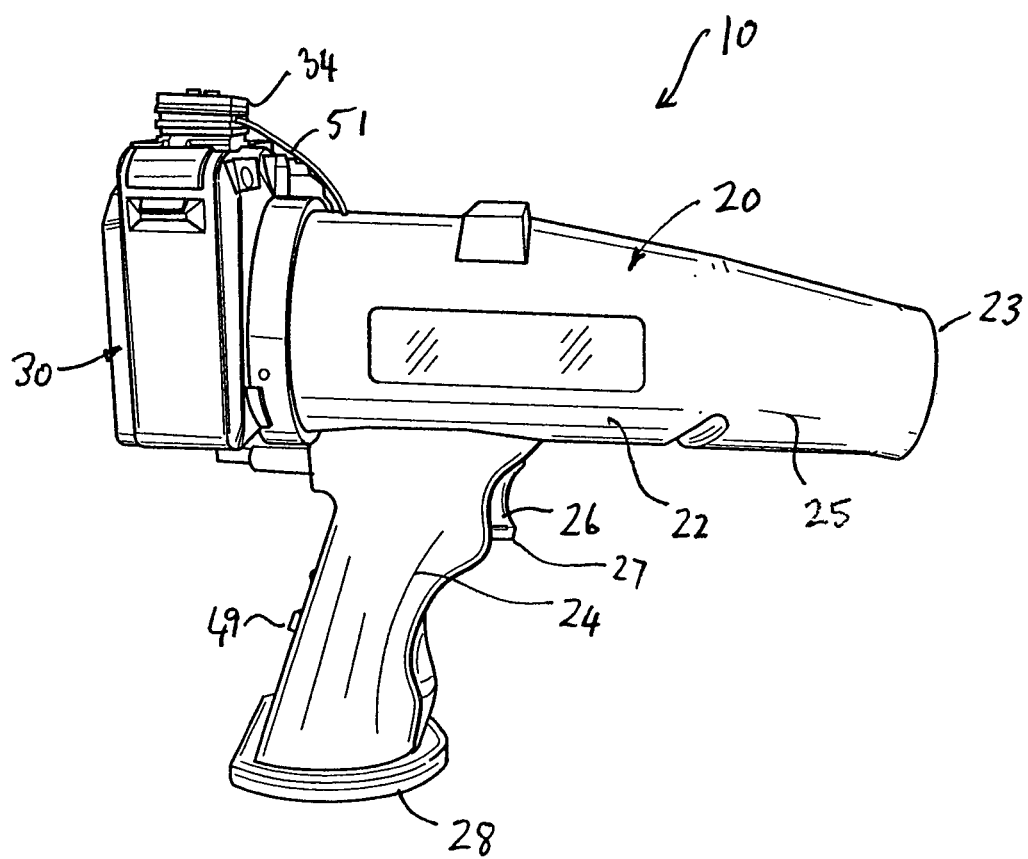
FIG. 1 is a perspective view of a self-contained retinal photography unit comprising an embodiment of optical apparatus in accordance with the invention.

The illustrated retinal photography unit 10 includes an integral molded housing 20 coupled to a digital camera 30. Housing 20 is moulded in a suitable plastics material and has two principal parts: a part conical generally tubular portion 22, and a depending handle 24 at the rear end of the tubular portion 22. Housing tubular portion 22 embraces camera lens assembly 32, projects forwardly from the camera to a front end or tip 23 and defines an optical path 21 aligned with the camera lens assembly and extending therefrom to tip 23 through adjacent nose region 25.

Handle 24 is dimensioned and profiled to be grasped by and thereby held in one hand with nose region 25 projecting forwardly from the hand. It will be appreciated that the housing has an appearance and size not dissimilar to a portable hand-held power drill or hairdryer and indeed a key advantage of the invention is that the apparatus is small, lightweight, portable and highly manipulable in the same fashion as a hand-held power drill or hairdryer. Further extending the analogy, handle 24 has a depressible spring-loaded finger trigger 26 on its front face for a purpose to be described, and a flat footplate 28 at its outer end by which the unit can be stood upright, in the position depicted in FIG. 1, on a table surface or the like.

Digital camera 30 is any suitable proprietary digital camera. An advantage of the apparatus is that the use of a standard digital camera enhances the familiarity of the unit and makes available all of the familiar standard functions of a digital camera. Such features includes a memory stick, a USB communication with a computer to download images when required, video mode, ability to review and delete images on the spot, etc.

In this embodiment, the unit is supplied with camera 30 built in. Other embodiments may not include the camera but be supplied as an accessory adapted to be fitted to the user's own camera.

Figures 2, 3:
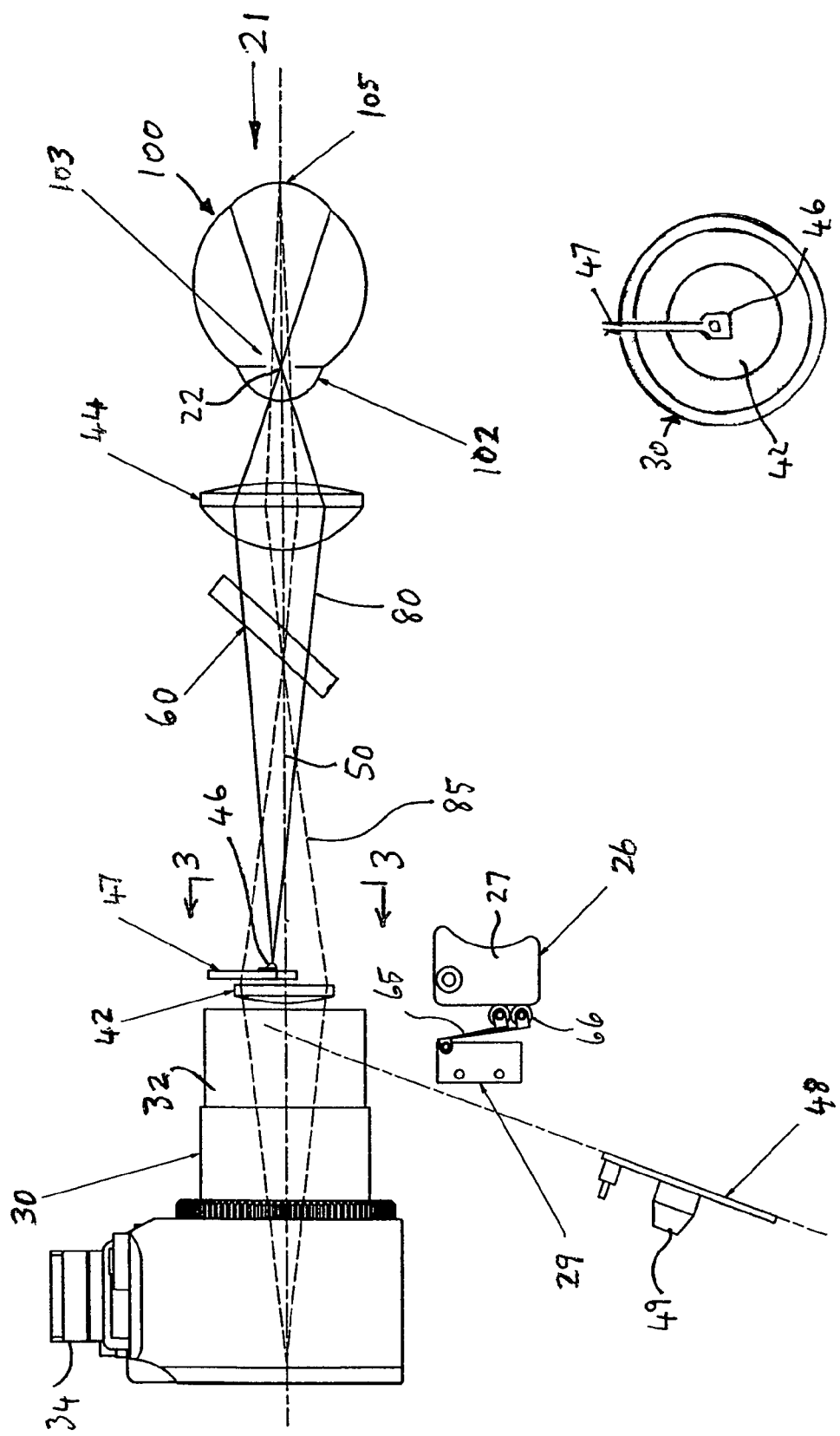
FIG. 2 is an optical ray diagram of the principal components of the self-contained retinal photography unit depicted in FIG. 1.
FIG. 3 is a cross section on the line 3-3 in FIG. 2.

Turning to FIG. 2 in particular, the optical path 21, which is effectively an elongate hollow interior of housing tubular portion 22, has mounted along its length four principal optical components. At the rear of housing tubular portion 22, and indeed forming a window at the rear end of optical path 21, is a convex lens 42. In the nose region 25 of the housing 20, forming a window at end or tip 23, is a double aspheric lens 44. Positioned immediately in front of rear lens 42 and on or near optical axis 50, is a solid state light source in the form of a light emitting diode (LED) 46. LED 46 needs to be small (e.g. about 2 mm in diameter) and mounted on a narrow stalk 47 (best appreciated from FIG. 3) so as to minimise the proportion of light returning to the camera that is blocked by the LED installation. Stalk 47 may be made of appropriately shaped circuit board.

FIG. 2 indicates the working position of the retina photography unit 10, in which it is placed in front of and pointed at a subject eye 100 having a cornea 102, pupil 103 and retina 105. Double aspheric front lens 44 is typically between 30 and 50 diopters, and is of a similar design to lenses normally used to view the retina. The diameter of this lens may, for example, be 30 to 50 mm. The distance from LED 46 to lens 44 is such that the light 80 from LED 46 is focused to a point 22 at or near the pupil of the eye. In this embodiment, this distance is approximately 90 to 120 mm, in which case the eye is ideally aligned with the pupil 30 to 50 mm from lens 44.

In general, rear lens 42 is selected to reduce the field of view of the digital camera 30 to the pupil area, to keep the total length of the device to a minimum, and to ensure that the retina of an eye without refractive error is in the middle of the focus range of digital camera 30. The rear lens 42 of the illustrated embodiment is a convex lens with a focal length of 60 to 100 mm. This lens is preferably positioned immediately in front of the camera lens assembly when in its fully extended position and immediately behind the illumination LED 46. The diameter of lens 42 is approximately matched to the camera lens external diameter.

It will be appreciated that lenses 42,44 cooperate to image the retina 105 of the eye at the image sensor of the camera 30, as indicated by the broken dash lines 85 in FIG. 2.

The steady state level of the light emitted by LED 46 is adjusted by a potentiometer 49 mounted on a printed circuit board (PCB) 48 within the handle 24 and accessible at the rear of the handle, to a level that is high enough for the camera to show the features of the retina but not so bright as to make it uncomfortable for the person or animal whose eye is being viewed.

Trigger 26 is connected, via electronics on the PCB 48 within handle 24, and cabling 51 to activate the camera to take a retinal photo. The trigger 26 includes a finger pivotable element 27 and associated microswitch assembly 29, and is designed with a sensitivity to allow the camera to take the photo without jerking the alignment of the array of optical components. The spring-loading of the trigger is provided by a spring steel arm 65 with roller contacts 66 that abut element 27. The microswitch assembly 29 can be made two stage, so that a partial or half press activates the camera to set the correct automatic adjustments for the camera and/or to turn on the illumination LED 46. The full press activates the camera to initiate the flash unit 34 and record the image. In this latter respect, LED 46 is linked to the camera's flash port and trigger so that the LED flashes to a brighter level as the camera captures the image. The flash duration of the LED is typically 15 to 16 ms.

An adjustable iris 60 is mounted in the optical path between LED 46 and front lens 44. Iris 60 is user adjusted to minimise reflections back from the eye of the illumination light 80. The iris is tilted to prevent reflections from it going back to the camera and to provide an oval/elliptical aperture to match the aspect ratio of the camera image. Alternatively, the iris may comprise a slit with straight or curved edges that are tilted to alter the aperture size and shape. As depicted in FIG. 2, the iris is preferably approximately at a focal plane of the combination of the camera optics and rear lens 42, as this gives slightly better image clarity. In the present embodiment this is approximately 70 to 80 mm in front of rear lens 42.

The focus of the camera can be adjusted manually or automatically to account for myopic of hyperopic eyes. The illumination system and internal electronics are powered by a battery (not shown) which is preferably the same battery that powers the digital camera. For example, a battery for this dual purpose may be mounted within handle 24. It will thus be appreciated that the apparatus is completely autonomous and does not require any connection to external power, computer or screen. It may thus be brought to the subject and eliminates the traditional situation that the subject must not only come to the retinal camera but must be seated in a specific position, typically at a bench or table.

An important advantage of the illustrated and described apparatus is that, in addition to its light weight and true portability and flexibility, it is intended to be used in a non-mydriatic fashion, thus eliminating the disadvantage to the subject of being administered drops or drugs to induce dilation of the pupil.

It will be appreciated that, while the above-described embodiment is designed primarily for human use, the invention is entirely adaptable to veterinary applications.

The invention claimed is:

1. Optical apparatus for retinal photography comprising:
   a housing fitted to or adapted to be fitted to a camera and defining an optical path that is aligned with the camera lens assembly and extends therefrom to a nose region of the housing, said housing having a projecting handle dimensioned and profiled to be grasped by hand for holding the apparatus in one hand; and
   a plurality of lens components in said optical path and an illumination source that co-operate to illuminate a retina of an eye in front of said nose region of the housing, and to image the illuminated retina at the image sensor of the camera, wherein said lens components include first and second lens elements that are mounted at spaced locations in the optical path respectively nearer the camera lens assembly and further from the camera lens assembly and cooperate to limit the field of view of the camera to the pupil area of said eye,
   wherein said nose region ends at a tip of the housing directly in front of the lens elements and the camera lens assembly, and said illumination source is a solid state light source mounted in the optical path between said first and second lens elements but closer to the first lens element, in a manner whereby light emitted by the solid state light source is focused, by the second lens element, at or near the pupil of an eye in front of and spaced from said tip of the housing and thereby illuminates the retina of the eye.

2. Optical apparatus for retinal photography according to claim 1 wherein said second lens element is a double aspheric lens.

3. Optical apparatus for retinal photography, according to claim 1, wherein the housing fitted or adapted to be fitted to the camera is of such a size when fitted to the camera that it is able to be held in one hand and thereby brought to a subject and held and operated in front of an eye of the subject.

4. Optical apparatus for retinal photography, according to claim 1 further including a trigger to flash the illumination source as the camera operates to capture said image.

5. Optical apparatus for retinal photography according to claim 4, further including control means including said trigger arranged whereby the trigger is actuable to operate the camera and the camera flash simultaneously with said flashing of the solid state light source.

6. Optical apparatus for retinal photography according to claim 4, wherein the housing comprises a generally tubular or tubular/conical portion that defines the optical path and encloses the lens components and the illumination source, and wherein the projecting handle is a depending handle incorporating the trigger.

7. Optical apparatus for retinal photography according to claim 6 wherein said generally tubular or tubular/conical portion of the housing includes a window at the end thereof remote from the camera.

8. Optical apparatus for retinal photography according to claim 4, wherein the trigger is on the projecting handle.

9. Optical apparatus for retinal photography according to claim 1 wherein said illumination source is mounted on a narrow stalk at or near the optical axis defined by the components.

10. Optical apparatus for retinal photography, according to claim 1, wherein an adjustable iris is provided between the light source and the second lens.

11. Optical apparatus for retinal photography, according to claim 10, wherein said iris is angled to divert reflections from it returning to the camera.

12. Optical apparatus for retinal photography, according to claim 1 wherein the apparatus includes a digital camera.

13. Optical apparatus for retinal photography, comprising:
    a housing fitted or adapted to be fitted to a camera and defining an optical path that is aligned with the camera lens assembly and extends therefrom to a nose region of the housing;
    first and second lens elements mounted at spaced locations in the optical path respectively nearer the camera lens assembly and further from the camera lens assembly, wherein said nose region ends at a tip of the housing directly in front of the lens elements and the camera lens assembly; and
    a solid state light source mounted in the optical path between said first and second lens elements but closer to the first lens element, in a manner whereby light emitted by the solid state light source is focused, by the second lens element, proximate the pupil of an eye in front of and spaced from said tip of the housing and thereby illuminates the retina of the eye;
    wherein said first and second lens elements cooperate to limit the field of view of the camera to the pupil area of said eye, and to image the illuminated retina at the image sensor of the camera.

14. Optical apparatus for retinal photography according to claim 13 wherein said second lens element is a double aspheric lens.

15. Optical apparatus for retinal photography, according to claim 13, wherein the housing fitted or adapted to be fitted to the camera is of such a size when fitted to the camera that it is able to be held in one hand and thereby brought to a subject and held and operated in front of an eye of the subject.

16. Optical apparatus for retinal photography, according to claim 13 further including a trigger to flash the illumination source as the camera operates to capture said image.

17. Optical apparatus for retinal photography according to claim 16, further including control means including said trigger arranged whereby the trigger is actuable to operate the camera and the camera flash simultaneously with said flashing of the solid state light source.

18. Optical apparatus for retinal photography according to claim 16, wherein the housing comprises a generally tubular or tubular/conical portion that defines the optical path and encloses the lens components and the illumination source, and a depending handle portion incorporating the trigger and dimensioned and profiled to be grasped by one hand for holding the apparatus in one hand.

19. Optical apparatus for retinal photography according to claim 18 wherein said generally tubular or tubular/conical portion of the housing includes a window at the end thereof remote from the camera.

20. Optical apparatus for retinal photography according to claim 16, wherein the trigger is on the projecting handle.

21. Optical apparatus for retinal photography according to claim 13 wherein said illumination source is mounted on a narrow stalk at or near the optical axis defined by the components.

22. Optical apparatus for retinal photography, according to claim 13 wherein the apparatus includes a digital camera.

23. Optical apparatus for retinal photography, according to claim 13, wherein an adjustable iris is provided between the light source and the second lens.

24. Optical apparatus for retinal photography, according to claim 23, wherein said iris is angled to divert reflections from said eye returning to the camera.

* * * * *